US012622576B2

(12) United States Patent     (10) Patent No.:   US 12,622,576 B2

Vogt et al.                        (45) Date of Patent:     May 12, 2026

(54) DEVICE AND METHOD FOR APPLYING A PHARMACEUTICAL FLUID

(71) Applicant: Heraeus Medical GmbH, Wehrheim (DE)

(72) Inventors: Sebastian Vogt, Wehrheim (DE); Thomas Kluge, Wehrheim (DE)

(73) Assignee: Heraeus Medical GmbH, Wehrheim (DE)

( * ) Notice: Subject to any disclaimer, the term of this patent is extended or adjusted under 35 U.S.C. 154(b) by 952 days.

(21) Appl. No.: 17/814,385

(22) Filed: Jul. 22, 2022

(65) Prior Publication Data

US 2023/0033990 A1     Feb. 2, 2023

(30) Foreign Application Priority Data

Jul. 28, 2021    (EP) ..................................... 21188130

(51) Int. Cl.
*A61B 1/015*       (2006.01)
*A61B 1/018*       (2006.01)
(Continued)

(52) U.S. Cl.
CPC .............. *A61B 1/015* (2013.01); *A61B 1/018* (2013.01); *A61B 2017/044* (2013.01); *A61B 17/3472* (2013.01); *A61B 2017/561* (2013.01); *A61B 17/68* (2013.01); *A61B 17/7098* (2013.01); *A61B 17/8057* (2013.01);
(Continued)

(58) Field of Classification Search
CPC . A61B 17/3472; A61B 17/68; A61B 17/8057; A61B 17/7098; A61B 17/8605; A61B 2017/044; A61B 2017/561; A61B 2017/8655; A61M 2039/2406; A61M 2039/242; A61M 2039/248; A61M 39/24; A61M 2039/025; A61M 2039/2473; A61M 2039/2426; A61M 2005/3128; A61M 2039/2433; A61M 2039/2493; A61M 39/22; A61F 2/28

See application file for complete search history.

(56)             References Cited

U.S. PATENT DOCUMENTS 4,413,985 A * 11/1983 Wellner .............. A61M 27/006
                                        604/9
5,478,216 A * 12/1995 Neward .................. F04B 33/00
                                       417/440

(Continued)

FOREIGN PATENT DOCUMENTS

BR       MU9100119 U2     9/2012
DE         3508759 A1     10/1985
(Continued)

*Primary Examiner* — William R Carpenter
*Assistant Examiner* — Robert F Allen
(74) *Attorney, Agent, or Firm* — Dicke, Billig & Czaja, PLLC

(57)             ABSTRACT

A device and method for applying a pharmaceutical fluid comprising a hollow cylindrical body, which surrounds a channel that extends through the body from a proximal body end to a distal body end of the body, wherein an outer surface of the body has at least partially an external thread, and has a connecting element arranged at the proximal body end, via which a proximal channel end of the channel can be reversibly connected in terms of fluid conduction to a reservoir for the pharmaceutical fluid.

13 Claims, 6 Drawing Sheets

(51) Int. Cl.

| | | |
|---|---|---|
| *A61B 17/04* | (2006.01) |
| *A61B 17/56* | (2006.01) |
| *A61B 17/80* | (2006.01) |
| *A61B 17/86* | (2006.01) |
| *A61M 5/142* | (2006.01) |
| *A61M 5/31* | (2006.01) |
| *A61M 39/02* | (2006.01) |
| *A61M 39/22* | (2006.01) |
| *A61M 39/24* | (2006.01) |
| *A61B 17/34* | (2006.01) |
| *A61B 17/68* | (2006.01) |
| *A61B 17/70* | (2006.01) |
| *A61B 17/88* | (2006.01) |
| *A61F 2/28* | (2006.01) |
| *A61F 2/30* | (2006.01) |
| *A61M 25/00* | (2006.01) |

(52) U.S. Cl.

CPC ... *A61B 17/8605* (2013.01); *A61B 2017/8655* (2013.01); *A61B 17/8805* (2013.01); *A61B 17/8811* (2013.01); *A61F 2/28* (2013.01); *A61F 2002/30143* (2013.01); *A61M 5/14276* (2013.01); *A61M 2005/3128* (2013.01); *A61M 25/007* (2013.01); *A61M 2039/025* (2013.01); *A61M 39/22* (2013.01); *A61M 2039/2426* (2013.01); *A61M 2039/2433* (2013.01); *A61M 2039/2473* (2013.01); *A61M 2039/2493* (2013.01); *A61M 2210/02* (2013.01)

(56) References Cited

U.S. PATENT DOCUMENTS

| | | | | |
|---|---|---|---|---|
| 5,571,139 A | * | 11/1996 | Jenkins, Jr. | A61B 17/0401 |
| | | | | 606/232 |
| 7,175,626 B2 | * | 2/2007 | Neff | A61B 17/8875 |
| | | | | 606/86 A |
| 7,717,947 B1 | * | 5/2010 | Wilberg | A61B 17/864 |
| | | | | 606/304 |
| 9,616,205 B2 | | 4/2017 | Nebosky et al. | |
| 10,357,298 B2 | | 7/2019 | Nebosky et al. | |
| 2004/0215155 A1 | * | 10/2004 | Wolfe | A61M 35/00 |
| | | | | 604/289 |
| 2005/0015059 A1 | * | 1/2005 | Sweeney | A61B 17/864 |
| | | | | 606/53 |
| 2006/0089647 A1 | * | 4/2006 | Culbert | A61B 17/742 |
| | | | | 606/65 |
| 2007/0233071 A1 | * | 10/2007 | Dewey | A61B 17/866 |
| | | | | 606/86 A |
| 2008/0039846 A1 | * | 2/2008 | Lee | A61B 17/686 |
| | | | | 433/7 |
| 2010/0030135 A1 | * | 2/2010 | Mitchell | A61M 31/00 |
| | | | | 606/305 |
| 2010/0042215 A1 | * | 2/2010 | Stalcup | A61B 17/866 |
| | | | | 606/86 R |
| 2011/0060373 A1 | * | 3/2011 | Russell | A61B 17/0401 |
| | | | | 606/86 R |
| 2012/0316571 A1 | * | 12/2012 | Sharkey | A61F 2/3859 |
| | | | | 623/18.11 |
| 2013/0096634 A1 | * | 4/2013 | Suh | A61B 17/8841 |
| | | | | 606/305 |
| 2013/0144344 A1 | * | 6/2013 | Giancola | A61B 17/742 |
| | | | | 606/304 |
| 2013/0184619 A1 | * | 7/2013 | Von Hollen | A61M 16/00 |
| | | | | 601/46 |
| 2014/0276347 A1 | * | 9/2014 | Stone | A61M 27/002 |
| | | | | 604/9 |
| 2015/0065992 A1 | * | 3/2015 | Korkuch | A61M 5/31511 |
| | | | | 604/193 |
| 2015/0080794 A1 | * | 3/2015 | Duong | A61M 25/10186 |
| | | | | 604/97.03 |
| 2015/0080813 A1 | | 3/2015 | Crawford et al. | |
| 2015/0122369 A1 | * | 5/2015 | Py | A61M 39/26 |
| | | | | 141/1 |
| 2018/0014867 A1 | | 1/2018 | Mazel | |
| 2018/0239370 A1 | * | 8/2018 | Perry, Jr. | A61M 5/3134 |
| 2019/0167326 A1 | * | 6/2019 | Greenhalgh | A61B 17/8605 |
| 2022/0134077 A1 | * | 5/2022 | Drew | A61M 39/0208 |
| | | | | 604/175 |
| 2022/0160965 A1 | * | 5/2022 | Kim | A61M 5/3007 |

FOREIGN PATENT DOCUMENTS

| | | |
|---|---|---|
| DE | 19949285 C2 | 8/2002 |
| DE | 102011112890 B4 | 6/2019 |
| EP | 1210019 B2 | 7/2009 |
| EP | 2887899 B1 | 8/2017 |

* cited by examiner

700

710

720

730

740

750

760

DEVICE AND METHOD FOR APPLYING A PHARMACEUTICAL FLUID

CROSS-REFERENCE TO RELATED APPLICATIONS

This application claims priority pursuant to 35 U.S.C. 119(a) to European Patent Application No. 21188130.5, filed Jul. 28, 2021, which application is incorporated herein by reference in its entirety.

BACKGROUND OF THE INVENTION

The invention relates to a device for applying a pharmaceutical fluid comprising a hollow cylindrical body, which surrounds a channel that extends through the body from a proximal body end to a distal body end of the body, wherein an outer surface of the body has at least partially an external thread, and comprising a connecting element arranged at the proximal body end, via which a proximal channel end of the channel can be reversibly connected in terms of fluid conduction to a reservoir for the pharmaceutical fluid.

The invention further relates to a method for applying a pharmaceutical fluid by means of such a device.

The subject matter of the invention is in particular a medical device for the temporary, the local application of pharmaceutical fluids or other medical fluids over a period of hours up to several months. The device according to the invention is particularly intended for the treatment of inflammatory diseases of joints, such as activated osteoarthritis and rheumatoid arthritis.

Inflammatory diseases of the joints, such as activated osteoarthritis and rheumatoid arthritis, are widespread. Such diseases are frequently associated with joint pain and can cause increasing joint destruction due to a progressive inflammation process, which can lead to an impairment of joint function or even to a complete loss of joint function.

In addition to a systemic pharmacological therapy option, which can be associated with side effects for the patient and which is less effective due to a comparatively low active ingredient concentration at the inflammation site, there is the possibility of influencing the inflammation process by intra-articular injection of pharmaceutical fluids, in particular anti-inflammatory active ingredients. For example, dexamethasone phosphate, cyclosporine, sulfasalazine and methotrexate can be considered as active ingredients in this case.

It is critical in intra-articular injection that there is a not insignificant risk of infection for the intra-articular space. Furthermore, the joint capsules of humans are equipped with nociceptors, whereby the joint capsules are very sensitive to pain.

Bone screws with a central channel in the screw body and outlet openings connected thereto are known under the name of cannulated and fenestrated screws. Up to now, such bone screws have been used substantially in the spine region as so-called cannulated and fenestrated pedicle screws. In this case, bone cement paste is injected through the channel of the screws into the mostly osteoporotic vertebral bodies, as a result of which a cement casing coaxial with the longitudinal axis of the pedicle screw is predominantly formed. The bone cement then hardens and forms an abutment for the pedicle screws. A large number of cannulated and fenestrated bone screws have been proposed. By way of example, the patent specifications and published patent applications DE 35 08 759 A1, DE 1994 9285 C2, DE 10 2011 112 890 B4, EP 1 210 019 B1, EP 2 887 899 B1 are cited.

In addition, cannulated and fenestrated bone screws can also be used for the local application of pharmaceutical fluids, as was described by way of example in the patent specifications and published patent applications U.S. Pat. No. 9,616,205 B2, U.S. Pat. No. 10,357,298 B2 and US 2018/0014867 A1.

A disadvantage of the previously described cannulated and fenestrated bone screws is an ingrowth of tissue, in particular of connective tissue, into the discharging openings of the bone screws, which impedes or even completely prevents further application of pharmaceutical fluids by means of the bone screw closed in this way in terms of fluid conduction.

Therefore, what is desirable is a device that is protected against the ingrowth of tissue, in particular of connective tissue, such that an application of a pharmaceutical fluid over a longer period of time, for example over several weeks or even months, is possible. The device should also allow a local application of any desired active pharmaceutical ingredients in the form of pharmaceutical fluids, wherein it is possible at any time to exchange the composition and/or the concentration of active ingredients in the pharmaceutical fluid. Moreover, it is desirable that the active ingredient concentration in the pharmaceutical fluid that is achieved immediately at the implantation site of the device be adjustable directly from the outside.

It is an object of the present invention to at least partially overcome one or more of the disadvantages resulting from the prior art.

In particular, a device for the local application of pharmaceutical fluids, such as, for example, antiphlogistic, cytostatic and glucocorticoid solutions, is to be provided, with which a local and temporary delivery of the pharmaceutical fluid into joint capsules of a patient, in particular joint capsules of larger joints, such as for example the knee joint, is made possible.

The device should be created in such a way that pharmaceutical fluids of any desired and changing composition can be introduced into the patient's joint capsule several times from outside the patient's body as required, without the joint capsule having to be punctured. The device should also be suitable for the repeated delivery of the pharmaceutical fluid over longer periods of time, for example over a period of several weeks or several months in the patient, without the device having to be removed for this purpose and without the obstruction of the device, in particular by deposition of endogenous tissue, in particular endogenous proteins. Furthermore, synovial fluid should not escape from the joint capsule through the device. The structure of the device should prevent microorganisms from penetrating into the intra-articular space. The device should be inexpensive to manufacture and as far as possible be a hygienic, disposable product that can only be used once. The fluid delivery from the device should be able to be controlled from the outside.

It is a further object of the invention to provide a method by means of which a locally limited application of pharmaceutical fluids is possible by means of which at least some of the objects already described are at least partially solved.

A contribution to at least partial fulfillment of at least one of the aforementioned objects is achieved via the features of the independent claims. The dependent claims provide preferred embodiments that contribute to at least partially fulfillment of at least one of the objects.

A first embodiment of the invention is a device for applying a pharmaceutical fluid comprising a hollow cylindrical body, which surrounds a channel that extends through the body from a proximal body end to a distal body end of the body, wherein an outer surface of the body has at least partially an external thread, and comprising a connecting element arranged at the proximal body end, via which a proximal channel end of the channel can be reversibly connected in terms of fluid conduction to a reservoir for the pharmaceutical fluid, characterized by a check valve that is arranged in the channel and is configured to be fluid-impermeable in the direction of the proximal channel end, and a sealing element arranged in the channel distal to the check valve, which closes a distal channel end of the channel in terms of fluid conduction and which has a gap that can be reversibly opened in terms of fluid conduction when pressure is applied to the pharmaceutical fluid from the direction of the proximal channel end, such that the pharmaceutical fluid can be applied from the distal channel end.

In one embodiment of the device, the gap reversibly opens in terms of fluid conduction upon the application of pressure of greater than 5 $N/cm^2$, preferably greater than 6 $N/cm^2$, more preferably greater than 7 $N/cm^2$, such that the distal channel end is open in terms of fluid conduction. This embodiment is a second embodiment of the invention, which is preferably dependent on the first embodiment of the invention.

In one embodiment of the device, the check valve comprises, in particular is, a ball check valve comprising a ball and a restoring element. This embodiment is a third embodiment of the invention, which is preferably dependent on the first or second embodiment of the invention.

In one embodiment of the device, the restoring element and the sealing element are configured in one piece. This embodiment is a fourth embodiment of the invention, which is preferably dependent on the third embodiment of the invention.

In one embodiment of the device, a filter element is arranged in the channel. This embodiment is a fifth embodiment of the invention, which is preferably dependent on one of the preceding embodiments of the invention.

In one embodiment of the device, the filter element is arranged in the channel proximal to the check valve, i.e. closer to the proximal channel end than the check valve. This embodiment is a sixth embodiment of the invention, which is preferably dependent on the fifth embodiment of the invention.

In one embodiment of the device, the filter element is a microporous filter plate. This embodiment is a seventh embodiment of the invention, which is preferably dependent on the fifth or the sixth embodiment of the invention.

In one embodiment of the device, the microporous filter plate has pores with an average pore diameter of less than 40 μm, preferably of less than 5 μm, more preferably of less than 1 μm. This embodiment is an eighth embodiment of the invention, which is preferably dependent on the seventh embodiment of the invention.

In one embodiment of the device, a hollow cylindrical sleeve is arranged in the channel distal to the sealing element, i.e. closer to the distal channel end than the sealing element, in order to prevent the discharging of the sealing element, and thus preferably also of all further structural elements in the channel proximal to the sealing element, from the distal channel end during the application of the pharmaceutical fluid. This embodiment is a ninth embodiment of the invention, which is preferably dependent on one of the preceding embodiments of the invention.

In one embodiment of the device, the proximal channel end is designed to be polygonal, in particular hexagonal, and the connecting element is equipped with a matching polygonal, in particular hexagonal, connecting element section, in order to reversibly connect in terms of fluid conduction the connecting element to the proximal channel end by inserting the connecting element section into the proximal channel end. This embodiment is a tenth embodiment of the invention, which is preferably dependent on one of the preceding embodiments of the invention.

In one embodiment of the device, the polygonal, in particular hexagonal, proximal channel end has a larger axial extension than the polygonal, in particular hexagonal, connecting element section, such that after removal, in particular by cutting off or sawing off, of a part, in particular a proximal part, of the proximal channel end, the connecting element can be reversibly connected in terms of fluid conduction to a part of the proximal channel end remaining on the device by inserting the connecting element section into the remaining proximal channel end. This embodiment is an eleventh embodiment of the invention, which is preferably dependent on the tenth embodiment of the invention.

In one embodiment of the device, the body comprises a metal, a polymer or a metal and a polymer, in particular the body consists of a metal, a polymer or a metal and a polymer. This embodiment is a twelfth embodiment of the invention, which is preferably dependent on one of the preceding embodiments of the invention.

A thirteenth embodiment of the invention is a method for applying a pharmaceutical fluid by means of a device according to one of the first to twelfth embodiments of the invention, comprising the following steps:

a. Implanting of the device;
b. Connecting in terms of fluid conduction of the device to a reservoir for the pharmaceutical fluid;
c. Building up of a conveyance pressure on the pharmaceutical fluid from the direction of the proximal channel end of greater than 5 $N/cm^2$;
d. Opening in terms of fluid conduction of the gap in the sealing element by the action of the conveyance pressure;
e. Dispensing of the pharmaceutical fluid from the gap that is open in terms of fluid conduction;
f. Closing in terms of fluid conduction of the gap by reducing the conveyance pressure to 5 $N/cm^2$ or less.

In the present description, range information also includes the values specified as limits. A specification of the type "in the range of X to Y" with respect to a variable A consequently means that A can assume the values X, Y, and values between X and Y. Ranges delimited at one end of the type "up to Y" for a variable A correspond accordingly to a value Y and less than Y.

Some of the described features are linked to the term "substantially". The term "substantially" is to be understood as meaning that, under real conditions and manufacturing techniques, a mathematically exact interpretation of concepts such as "superimposition", "perpendicular", "diameter" or "parallelism" can never apply exactly, but can only apply within certain manufacturing-related error tolerances. For example, "substantially perpendicular axes" include an angle of 85 degrees to 95 degrees relative to one another, and "substantially equal volumes" include a deviation of up to 5% by volume. A "device consisting substantially of plastic" comprises, for example, a plastic fraction of >95 to <100% by weight. A "substantially complete filling of a volume B" comprises, for example, a filling of >95 to <100% by volume of the total volume of B.

DETAILED DESCRIPTION

A first subject of the invention relates to a device for applying a pharmaceutical fluid, in particular for applying a pharmaceutical fluid into a joint capsule, comprising a hollow cylindrical body that surrounds a channel that extends through the body from a proximal body end to a distal body end of the body, wherein an outer surface of the body at least partially has an external thread, and comprising a connecting element arranged at the proximal body end, via which a proximal channel end of the channel can be reversibly connected in terms of fluid conduction to a reservoir for the pharmaceutical fluid, characterized by a check valve that is arranged in the channel and is configured to be fluid-impermeable in the direction of the proximal channel end, and a sealing element arranged in the channel distal to the check valve, which closes a distal channel end of the channel in terms of fluid conduction and in which a gap can be reversibly opened in terms of fluid conduction when pressure is applied to the pharmaceutical fluid from the direction of the proximal channel end, such that the pharmaceutical fluid can be applied from the distal channel end.

The device has a check valve in the channel. A check valve is a component that allows the pharmaceutical fluid to be conveyed in one conveying direction, while conveying in the opposite conveying direction is prevented. The check valve according to the invention allows the conveyance of the pharmaceutical fluid from the direction of the proximal channel end in the direction of the distal channel end, while the conveyance of the pharmaceutical fluid from the direction of the distal channel end in the direction of the proximal channel end is prevented. Thus, the check valve according to the invention is configured to be fluid-conducting in the direction of the distal channel end and fluid-impermeable in the direction of the proximal channel end. Thus, this enables the conveyance and application of a pharmaceutical fluid from a reservoir for the pharmaceutical fluid connected to the connecting element through the device and out of the distal channel end, while penetration of fluids, in particular fluids charged with connective tissue, into the channel proximal of the check valve is prevented. This prevents the, in particular complete, contamination and/or obstruction of the device and the reservoir connected to the device by a fluid, such as blood, penetrating into the distal channel end.

Distal to the check valve, i.e. closer to the distal channel end than the check valve, a sealing element is arranged in the channel, which sealing element closes the distal channel end in terms of fluid conduction until a gap in the sealing element opens in terms of fluid conduction, triggered by a sufficiently high application of pressure on the pharmaceutical fluid in the channel from the direction of the proximal channel end. If the application of pressure is not high enough, the gap remains closed in terms of fluid conduction. Upon continued application of pressure, the pharmaceutical fluid can be applied to a desired point from the channel through the gap that is open in terms of fluid conduction. When the application of pressure ceases, the previously formed gap that is open in terms of fluid conduction in the sealing element automatically closes again within a few moments, for example within fractions of one second, and the distal channel end is again closed in terms of fluid conduction by the sealing element. For this purpose, the sealing element is preferably made of an elastic material. As a result of the sealing element, the ingrowth of connective tissue and penetration of blood into the device is prevented, which is why the device can remain functionally implanted in the patient's body over several days to months, allowing a repeated local application of a pharmaceutical fluid at the desired site in the patient. A further advantage of the structure of the device is that, even if the distal channel end were to become obstructed in terms of fluid conduction, for example by connective tissue or clotted blood, such obstruction would be eliminated by the application of pressure and the subsequent delivery of the pharmaceutical fluid from the device under pressure. Thus, the structure and the mode of operation of the device enables a "self-cleaning" of the obstruction through the use of the device.

For this purpose, the sealing element can have one or more than one gap, wherein the one or more than one gap can have different shapes. Due to the simple production method, a single, elongated gap is preferred.

The device can be operated in at least two ways. In a first way, the application of pressure is performed in a pulsed manner, such that an internal pressure generated by the application of pressure decreases as a result of applying a small amount of pharmaceutical fluid, for example up to 2 milliliters, from the device in such a way that the gap is closed in terms of fluid conduction again. The application of pressure in this case only reaches a required limit value in order to make the gap reversibly fluid-conductive for a short time, i.e. in a pulsed manner. In a further way, a continuous application of pressure to the pharmaceutical fluid takes place, such that it can be discharged from the distal channel end as long as the application of pressure at the required limit value is maintained. This way of applying pressure thus enables a continuous application of a pharmaceutical fluid.

Should fluid charged with connective tissue penetrate into the distal channel end in spite of the sealing element, the check valve serves as a second barrier for the penetrating fluid. Thus, the sealing element and check valve thus interact synergistically, such that contamination of the device is effectively prevented. This allows the device to remain implanted over a longer period than a device with only one barrier.

The check valve can have different structural shapes. In one embodiment, the check valve comprises a check valve flap that allows the pharmaceutical fluid to be conveyed through the channel only in one conveying direction and closes the channel in terms of fluid conduction in the opposite conveying direction.

The device comprises a hollow cylindrical body. "Hollow cylindrical body" is understood to mean a tubular structural element that surrounds a channel with an inner surface facing the channel and an outer surface facing away from the channel. The cross-section of the body can take any shape. Due to the simple manufacture and the better anchoring capability within a patient, the cross-section, and preferably also the cross-section of the channel, is substantially circular.

The channel extends from a proximal body end of the body through the body to a distal body end of the body. A proximal channel end of the channel faces the proximal body end, and a distal channel end of the channel faces the distal body end.

"Proximal" and "distal" merely serve to designate the spatially opposite ends of the device, of the body or of other structural units of the device, and do not allow the orientation of the device implanted in a human body to be deduced. "Distal to . . . " and "proximal to" or similar formulations accordingly express only the spatial arrangement of two structural units of the device relative to one another.

The outer surface of the body has an external thread at least in sections. The external thread serves to anchor the device in a tissue, in particular a bone tissue of a patient, by screwing the device into a corresponding prepared borehole in the tissue, in particular in the bone tissue. In one embodiment, the external thread extends over the entire axial extension of the body, such that the body can be screwed into the corresponding borehole over its entire length. In this case, the external thread can be arranged on an outer side of a tubular element, which surrounds the body in the manner of a cuff. In a preferred embodiment, the outer surface of the body itself is formed as an external thread.

The device has a fluid-conducting connecting element at the proximal body end, via which the proximal channel end can be reversibly connected in terms of fluid conduction to a reservoir for the pharmaceutical fluid. In one embodiment, the connecting element and the proximal body end are configured in one piece. In further preferred embodiments, the connecting element and the distal body end are reversibly connectable to one another in terms of fluid conduction. The connecting element can be configured in different ways in order to connect the proximal channel end in terms of fluid conduction to a reservoir for a pharmaceutical fluid. In one embodiment, the connecting element is formed as a grommet, via which the proximal channel end can be connected in terms of fluid conduction to a reservoir by means of a tube. In a further embodiment, the connecting element is shaped as a thread, which can be connected in terms of fluid conduction to a reservoir via a corresponding counterpart. In a further embodiment, the connecting element forms a flange connection with a reservoir. In a further embodiment, the connecting element forms a fluid-conducting connection with a reservoir via a tube coupling, wherein the connecting element can have the coupling or the nipple of the tube coupling.

The term "reservoir" is understood to mean all containers that are suitable for storing a pharmaceutical fluid. Examples of reservoirs include bags, syringes, flasks, balloons, canisters and ampules, wherein bags, balloons and syringes are preferred.

The device according to the invention serves the purpose of the local application of a pharmaceutical fluid, in particular for the treatment of inflammatory diseases of joints, such as activated osteoarthritis and rheumatoid arthritis, over a period of several days to several months. A pharmaceutical fluid contains at least one active pharmaceutical ingredient. For example, the pharmaceutical fluid is an aqueous or non-aqueous solution or suspension of active pharmaceutical ingredients.

In one embodiment, the pharmaceutical fluid comprises solutions that contain at least one antiphlogistic, cytostatic and/or glucocorticoid. In a further embodiment, the pharmaceutical fluids contain at least one disinfectant component.

Furthermore, pharmaceutical fluids also comprise gases, gas mixtures and solutions of gases in liquids, for example water.

The application of pressure to the pharmaceutical fluid necessary to form the gap in the sealing element that is open in terms of fluid conduction can depend on different factors, such as, for example, the material of the sealing element, the diameter of the sealing element and the length of the sealing element.

In order to provide a controlled application of the pharmaceutical fluid from the device, one embodiment of the device is characterized in that the gap reversibly opens in terms of fluid conduction in the sealing element only starting at an application of pressure of at least 5 $N/cm^2$ on the pharmaceutical fluid from the direction of the proximal channel end, such that the distal channel end is opened in terms of fluid conduction. If the application of pressure does not reach said limit value, the gap and thus the distal channel end remain closed in terms of fluid conduction. This prevents unintentional escape of the pharmaceutical fluid from the device into the patient, which could entail health risks. A further advantage is that a penetration of fluids of the patient that are charged with tissue, in particular with connective tissue, is thus not at least made more difficult without reaching a correspondingly opposed conveyance pressure in the direction of the proximal channel end into the device through the distal channel end. Penetration of such endogenous fluids could result in the contamination of the device or the obstruction of the device. To ensure that an application can take place in a controlled manner, even in small quantities and without the risk of unintentional destruction in the device, such as, for example, crack formation in the body or in the sealing element, it is preferred that the application of pressure must not be more than 150 $N/cm^2$ for the fluid-conducting opening of the gap.

The check valve can have different structural shapes. In one embodiment, the check valve comprises a check valve flap that allows the pharmaceutical fluid to be conveyed through the channel in only one conveying direction, in particular in the direction of the distal channel end, and closes the channel in terms of fluid conduction in the opposite conveying direction, in particular in the direction of the proximal channel end. In a further embodiment, the check valve is designed as a disk check valve.

One embodiment of the device is characterized in that the check valve is a ball check valve comprising a ball and a restoring element. With a ball check valve, a conduction means is closed in terms of fluid conduction by a ball, which is held against the conduction means by gravity, or as provided according to the invention, by a restoring element in order to close said conduction means in terms of fluid conduction. A fluid that is conveyed by the conduction means against the ball and the restoring element acting on the ball can open the ball check valve in terms of fluid conduction if the conveyance pressure outweighs the pressure of the restoring element on the ball. From the opposite conveying direction, i.e. from the direction of the restoring element in the direction of the conduction means, the ball check valve remains closed in terms of fluid conduction by the ball. An advantage of a ball check valve is the simple, cost-effective design and low susceptibility to malfunctions.

The restoring element can be configured in different ways, in order to press the ball against the conduction means and to close the ball check valve in terms of fluid conduction. In one embodiment, the restoring element comprises a spring, for example a spiral spring or leaf spring, for example consisting of a metal. In a further embodiment, the restoring element comprises an elastic polymer element, in particular a tubular or leaf-spring-like polymer element.

The restoring element can be present as a separate component or can be connected to further components of the device.

One embodiment of the device is characterized in that the restoring element and the sealing element are configured in one piece. This reduces the number of components of the device, which simplifies the manufacture thereof and also results in a reduction in the susceptibility to malfunctions. Since the sealing element is preferably made of an elastic material, the configuration of the end of the sealing element facing the check valve, in particular the ball of the ball check valve, as a restoring element, for example as an elastic tube piece or as elastic leaf spring elements, enables a simple and cost-effective design of the device.

In order to free the pharmaceutical fluid from any microorganisms that might be present, one embodiment of the device is characterized in that a filter element is arranged in the channel.

The filter element can be arranged at different locations within the channel.

In order to prevent the complete contamination of the device, for example by microorganisms, one embodiment of the device is characterized in that the filter element is arranged in the channel proximally to the check valve, i.e. closer to the proximal channel end than the check valve. In this embodiment of the device, the pharmaceutical fluid passes through the filter element first of all, followed by the check valve and finally the sealing element, when conveyed through the channel from the direction of the proximal channel end. Thus, when the pharmaceutical fluid is applied, filtration through the filter element is carried out before the pharmaceutical fluid reaches the check valve and the sealing element.

The filter element can be configured differently. In one embodiment, the filter element comprises a nonwoven, in particular a glass fiber mat. In a further embodiment, the filter element comprises a fiber material, in particular a polyester, metal and/or a cellulose fiber material. In a further embodiment, the filter element comprises a wire mesh, in particular a stainless steel wire mesh.

One embodiment of the device is characterized in that the filter element comprises a microporous filter plate, in particular that the filter element is a microporous filter plate.

The microporous filter plate can have pores with average pore diameters of different sizes. An "average pore diameter" is understood to mean the arithmetic mean of the pore diameters of the pores of the filter plate.

One embodiment of the device is characterized in that the microporous filter plate has pores with an average pore diameter of less than 40 µm, preferably less than 5 µm, more preferably less than 1 µm. This enables the good cleaning of the pharmaceutical fluid. In order to ensure frictionless conveying of the pharmaceutical fluid through the device despite the good filtration performance, it is preferred that the average pore diameter is not less than 0.05 µm.

In order to prevent the discharging of the sealing element from the distal channel end during the application of a pharmaceutical fluid by means of the device, the sealing element can be fastened in different ways in the channel. In one embodiment, the sealing element is fixed within the channel by means of an adhesive.

One embodiment of the device is characterized in that a hollow cylindrical sleeve is arranged in the channel distal to the sealing element, i.e. closer to the distal channel end than the sealing element, in order to prevent the sealing element from being discharged from the distal channel end during the application of the pharmaceutical fluid. In order to fix the hollow cylindrical sleeve itself in the channel, it can interact with the inner surface of the body in a form-fitting and/or force-fitting manner by means of a tongue-and-groove connection, and can thus prevent discharge.

The connecting element and the hollow cylindrical body can be connected to one another in different ways in order to connect the connecting element and the proximal channel end in terms of fluid conduction. In one embodiment, the connecting element and the body are configured in one piece.

In further embodiments, the connecting element and the body are connected to one another by means of an adhesive connection, a bayonet connection or a threaded connection.

One embodiment of the device is characterized in that the proximal channel end is designed to be polygonal, in particular hexagonal, and the connecting element is equipped with a polygonal, in particular hexagonal, connecting element section, in order to reversibly connect in terms of fluid conduction the connecting element to the proximal channel end by inserting the connecting element section into the proximal channel end.

The insertion, i.e. pushing in of the connecting element section into the proximal channel end, enables a secure, simple and cost-effective option for fastening the connecting element to the proximal channel end. After insertion, the proximal channel end and the connecting element section interact in a form-fitting and/or force-fitting manner, but can also be released from one another again if required by pulling on the connecting element. This process can be repeated as frequently as desired. In order to connect the two components to one another securely in terms of fluid conduction, the connecting element and the proximal channel end preferably have the same number of edges and mutually matching edge dimensions, such that these can be pushed together in the manner of a "key-lock". An advantage of this is that an undesired axial rotation of the two components relative to one another is thus prevented and the device can be connected to a reservoir for a pharmaceutical fluid in a desired orientation. Another advantage is that the polygonal configuration of the proximal channel end allows the device to be screwed into a correspondingly prepared borehole in the bone tissue of a patient by means of a matching polygonal tool, in particular a key.

In order to enable the complete insertion of the polygonal connecting element section into the proximal channel end, it is preferred that the polygonal proximal channel end has at least the same axial extension as the polygonal connecting element section.

One embodiment of the device is characterized in that the polygonal proximal channel end has a larger axial extension than the polygonal connecting element section, such that, after the removal of a part of the proximal channel end, in particular by sawing or cutting off, the connecting element can be connected to a remaining part of the proximal channel end in terms of fluid conduction by inserting the connecting element section into the remaining proximal channel end.

The device can be implanted in different ways into the bone tissue of a patient. In order to ensure a mobility of the joint that is high as possible and thus a movement sequence that is as natural and pain-free as possible, it is preferred for the device to be countersunk as completely as possible in the bone tissue. Depending on the size of the patient and the thickness of the bone tissue present, it may be necessary to shorten the device for the most complete possible countersinking in the bone tissue.

If the axial extension, i.e. the length, of the polygonal proximal channel end is greater than the axial extension of the polygonal connecting element section, the proximal channel end can be shortened, for example by cutting off or sawing off, wherein, after the shortening of the proximal channel end, the connecting element section can still be pushed completely into the proximal channel end, in order to connect the connecting element to the channel in terms of fluid conduction.

In one embodiment of the device, the body comprises a metal, a polymer or a metal and a polymer, in particular the body consists of a metal, a polymer or a metal and a polymer. Examples of polymers include polyamides, polyesters, polyketones, polymethacrylates and copolymers thereof. Examples of metals include pure metals such as aluminum and titanium or metal alloys such as stainless steels, in particular stainless steel 1.4404, or titanium alloys such as $TiAl_6V_4$.

In order to control a proper and targeted application at the desired location within a patient, one embodiment of the device is characterized in that at least a portion of the device, in particular the hollow cylindrical body of the device, has an x-ray opacifier. By means of an x-ray opacifier, the correct positioning of the device within the patient can be visualized via imaging methods by means of x-ray radiation. Examples of x-ray opacifiers are barium sulfate, zirconium dioxide and calcium carbonate.

A further subject of the invention relates to a method for applying a pharmaceutical fluid by means of a device according to one of the preceding embodiments, comprising the following steps:

a. Implanting of the device;

b. Connecting in terms of fluid conduction of the device to a reservoir for the pharmaceutical fluid;

c. Building up of a conveyance pressure on the pharmaceutical fluid from the direction of the proximal channel end of greater than 5 $N/cm^2$;

d. Opening in terms of fluid conduction of the gap in the sealing element by the action of the conveyance pressure;

e. Dispensing of the pharmaceutical fluid from the gap that is open in terms of fluid conduction;

f. Closing in terms of fluid conduction of the gap by reducing the conveyance pressure to 5 $N/cm^2$ or less.

The implantation of the device in the patient can take place in different ways. In a preferred embodiment, the implantation is carried out by screwing the device into a borehole prepared for this purpose in the bone tissue of the patient. The implantation preferably takes place in spatial proximity to a joint capsule, such that pharmaceutical fluid applied by means of the device can reach the corresponding joint space. In order to prevent complications and potential infections of the joint, the device is preferably implanted in such a way that the joint capsule is not perforated. For example, the device for treating a knee joint can be inserted into a borehole in the distal femur, wherein the borehole ends in the intercondylar space. In order to achieve the secure fixing of the device in the bone tissue, a diameter of the borehole is selected such that the device can be screwed into the borehole in a substantially gap-free manner.

The length of the borehole can be determined graphically by x-ray, such that the device can be shortened prior to implantation if necessary.

Preferably, the device is screwed into the borehole until the proximal body end terminates closely below, for example 1 mm below, the corresponding joint surface. This ensures a largely normal movement sequence of the corresponding joint.

After implantation, the device is connected in terms of fluid conduction to a reservoir for the pharmaceutical fluid. The fluid-conducting connection can be realized in different ways, wherein it is preferred to connect the device and the reservoir in terms of fluid conduction by means of a flexible tube. In order to connect the tube to the reservoir in terms of fluid conduction, an adapter, in particular a Luer system with a cover cap, can be used, for example. In this way, pharmaceutical fluids can be introduced into the intra-articular space to be treated at any time as required with a simple syringe.

In order to prevent contamination with microorganisms, it is preferred to equip the tube with a sterile filter.

In order to apply the pharmaceutical fluid from the device, in particular the distal channel end, a conveyance pressure is built up onto the pharmaceutical fluid, which pressure acts from the direction of the proximal channel end in the direction of the distal channel end. The conveyance pressure conveys the pharmaceutical fluid from the reservoir into the proximal channel end of the device, through the check valve and the sealing element, and ultimately out of the distal channel end. In order to pass through the check valve and in particular also the sealing element, a conveyance pressure of at least 5 $N/cm^2$ is exerted on the pharmaceutical fluid. This conveyance pressure is sufficient to reversibly open the gap in the sealing element in terms of fluid conduction and thus to allow the pharmaceutical fluid to flow out of the device, in particular the distal channel end.

The conveyance pressure on the pharmaceutical fluid to form the gap that is open in terms of fluid conduction in the sealing element can be exerted in different ways. In one embodiment, the conveyance pressure is exerted by means of a separate pump, for example a peristaltic pump, which acts on a tube inserted as a fluid-conducting connection between the device and the reservoir. In a further embodiment, the reservoir for the pharmaceutical fluid is a syringe, and the conveyance pressure on the pharmaceutical fluid is exerted by means of a syringe plunger belonging to the syringe.

If the conveyance pressure is reduced to 5 $N/cm^2$ or less, the gap in the sealing element is automatically closed within a few moments, for example within one second or shorter, and the application of the pharmaceutical fluid is terminated.

The features disclosed for the device are also disclosed for the method, and vice versa.

The invention is illustrated by way of example below by means of figures. The invention is not limited to the figures. The following are shown:

FIG. 1 schematic longitudinal section of a device for applying a pharmaceutical fluid, FIG. 2 the device from FIG. 1 in a perspective side view of a partial schematic longitudinal section of one, FIG. 3 the device from FIGS. 1 and 2, with pharmaceutical fluid being conveyed, FIG. 4 the device from FIGS. 1 to 3, during application of the pharmaceutical fluid, FIG. 5 the device from FIGS. 1 to 4, connected in terms of fluid conduction to a reservoir for a pharmaceutical fluid, and FIG. 6 method for applying a pharmaceutical fluid.

Figure 1:
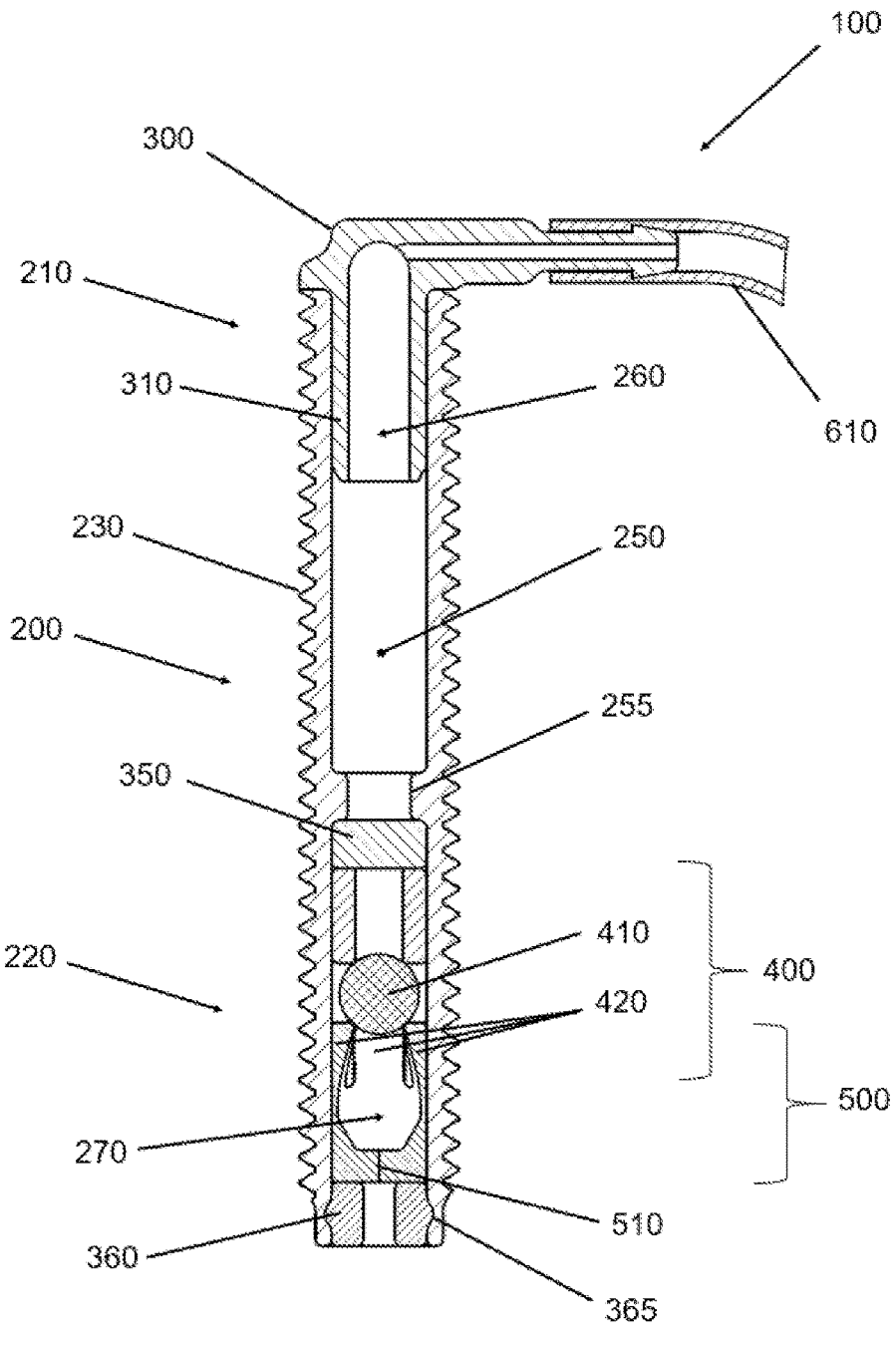
FIG. 1 shows a schematic longitudinal section of an exemplary embodiment of a device 100 for applying a pharmaceutical fluid (not shown in FIG. 1). The device 100 comprises a hollow cylindrical body 200 with a proximal body end 210 and a distal body end 220 axially opposite the proximal body end 210. An outer surface of the body 200 is formed as an external thread 230. In the embodiment of the device 100 shown, the external thread 230 extends over almost the entire length of the device 100. In further embodiments (not shown) of the device 100, the external thread 230 does not extend almost over the entire length, but for example only over 50% of the entire length of the device 100. The external thread 230 serves the purpose of screwing the device 100 into a borehole in the bone of a patient.

A fluid-conducting channel 250 runs axially through the hollow cylindrical body 200, wherein the channel 250 extends from a proximal channel end 260 facing the proximal body end 210 through the entire body 200 to a distal channel end 270 facing the distal body end 220. The proximal channel end 260 is connected in terms of fluid conduction to a connecting element 300, via which the device 100 is connected in terms of fluid conduction to a reservoir for a pharmaceutical fluid (neither shown in FIG. 1). In order to connect the connecting element 300 to the proximal channel end 260 in terms of fluid conduction, the connecting element 300 has a connecting element section 310 that is inserted into the proximal channel end 260. In the embodiment shown, the connecting element 300 is formed as a grommet, such that a reservoir for a pharmaceutical fluid can be connected in terms of fluid conduction to the device 100 by means of a tube 610 (only shown in sections).

A check valve 400 in the form of a ball check valve comprising a ball 410 and a restoring element 420 in the form of four elastic, leaf spring-shaped elements (only three of the elements are shown, the fourth is located outside the drawing plane) is arranged in the channel 250. The restoring element 420 exerts a force on the ball 410, such that the latter closes the check valve 400 in terms of fluid conduction. The check valve 400 is arranged in such a way that a fluid coming from the direction of the proximal channel end 260 can displace the ball 410 against the force of the restoring element 420 in the direction of the distal channel end 270, such that the check valve 400 is opened in terms of fluid conduction. In the opposite direction, i.e. from the distal channel end 270 in the direction of the proximal channel end 260, the check valve 400 remains closed in terms of fluid conduction and cannot be opened in a non-destructive manner.

Distal to the check valve 400, a sealing element 500 comprising a gap 510 that is closed in terms of fluid conduction is arranged within the channel 250. In the embodiment shown of the device 100, the restoring element 420 and the sealing element 500 are configured in one piece.

In order to protect the sealing element 500, and thus also the check valve 400, against unintentional discharging from the channel 250 during the application of a pharmaceutical fluid, a sleeve 360 is arranged distally to the sealing element 500, which sleeve 360 is fixed to the body 200 in the channel 250 via a tongue-and-groove connection 365.

A filter element 350 in the form of a microporous filter plate is arranged proximally of the check valve 400 in the channel 250, in order to clean a pharmaceutical fluid conveyed by the device 100 of microorganisms.

As a counterpart to the sleeve 360, the channel 250 has a channel constriction 255, such that the filter element 350, the check valve 400 and the sealing element 500 are fixed between the sleeve 360 and the channel constriction 255.

Figure 2:
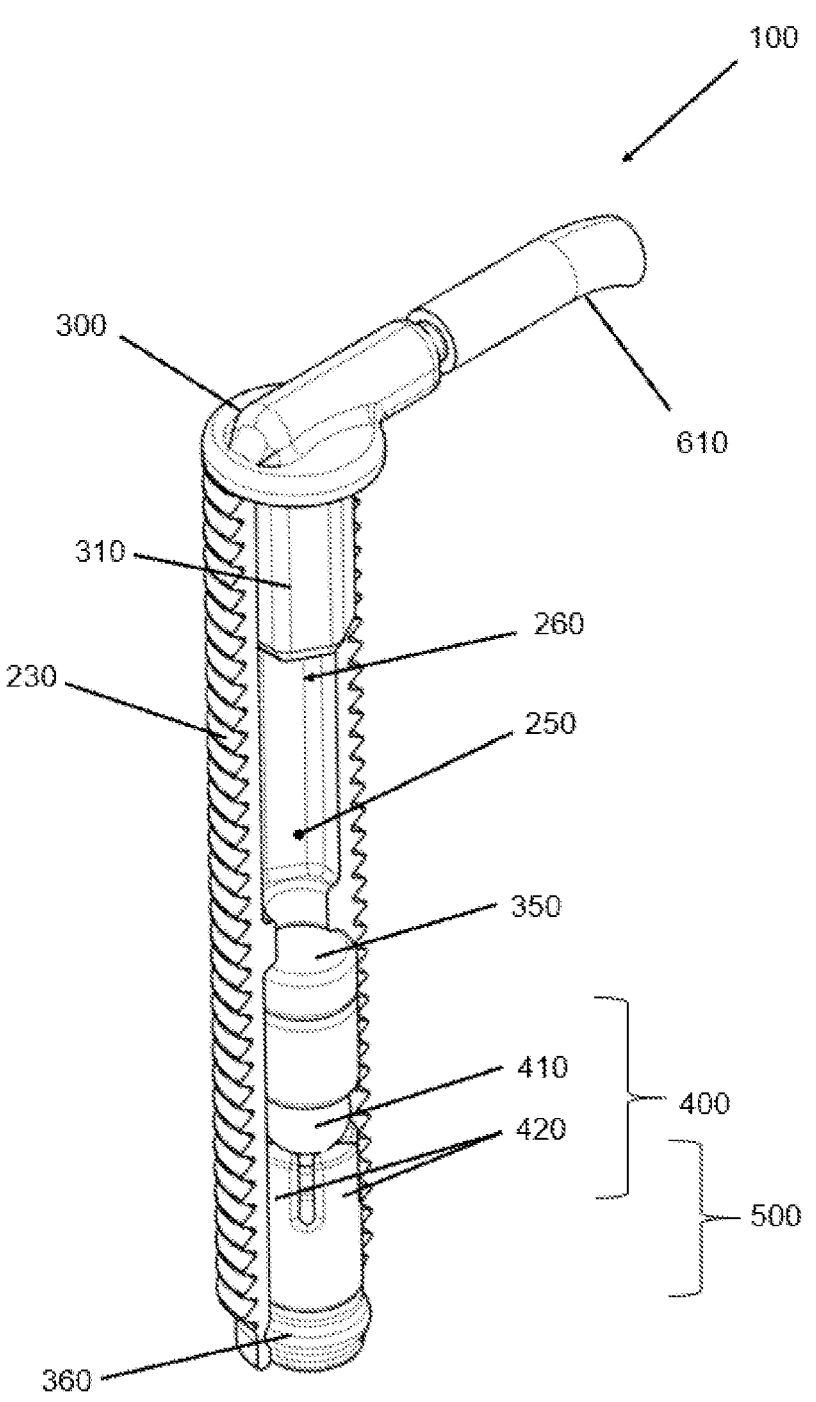

FIG. 2 shows the device 100 from FIG. 1 in a perspective side view of a partial schematic longitudinal section. For the design and arrangement of the individual structural features, reference is made to the statements regarding FIG. 1. In the perspective of the device 100 shown in FIG. 2, it can be seen that the connecting element section 310 and the proximal channel end 260 are configured to be polygonal, in particular hexagonal, such that the connecting element section 310 can be reversibly inserted into the proximal channel end 260 in a rotationally secure manner.

The polygonal proximal channel end 260 has a larger axial extension than the polygonal connecting element section 310. This enables the shortening of the proximal channel end 260, for example by sawing or cutting off, and a fluid-conducting connection of the connecting element section 310 to the rest of the proximal channel end 260 remaining after the shortening. The device 100 shortened in its overall length in this manner thus also enables implantation into bone tissue, which would have had insufficient thickness prior to shortening.

Figure 3:
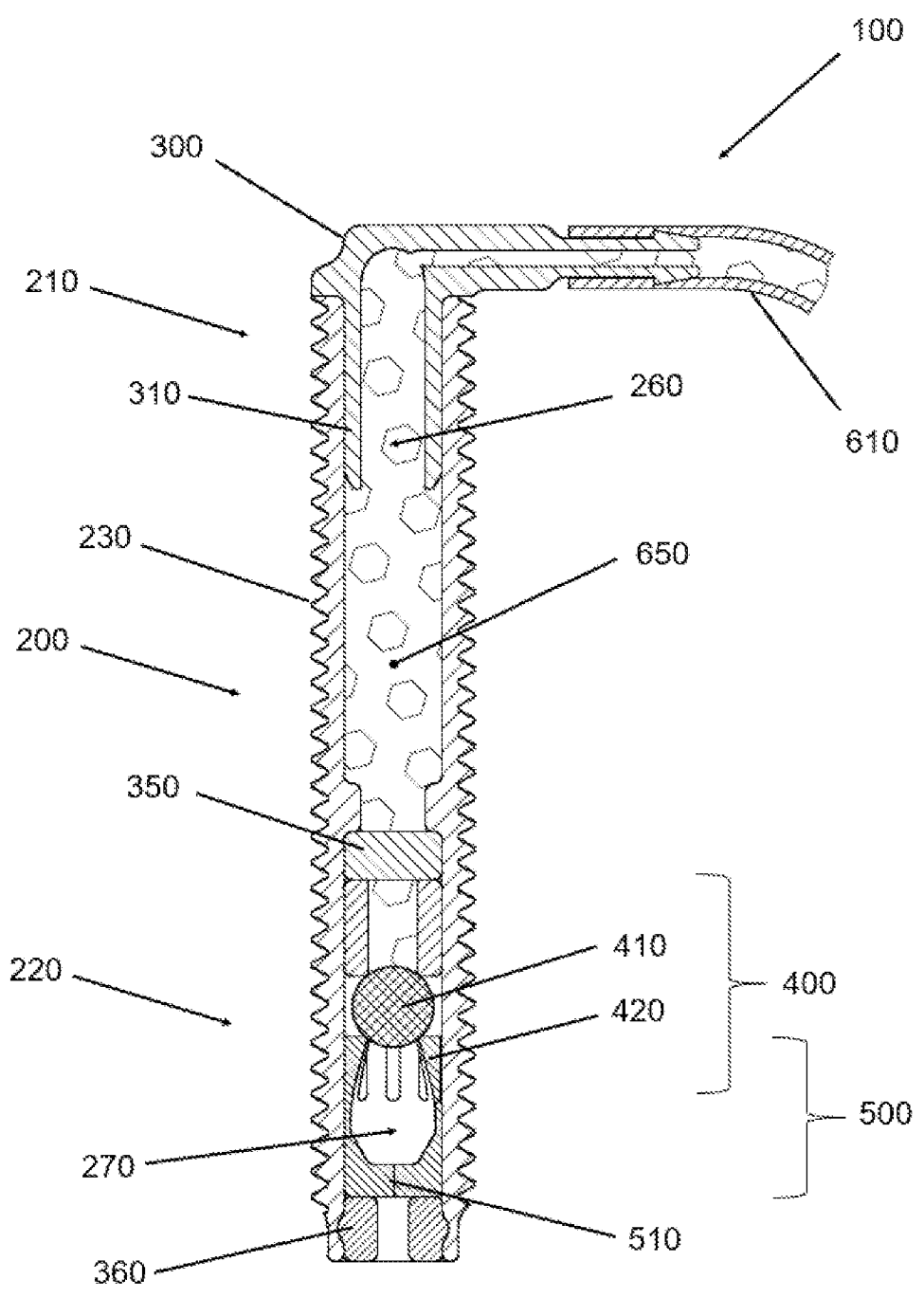

FIG. 3 shows the device 100 from FIGS. 1 and 2, wherein a pharmaceutical fluid 650 has been introduced via the tube 610 into the proximal channel end 260. The pharmaceutical fluid 650 fills the channel 250 from the proximal end 260 to the ball 410. In order to convey the pharmaceutical fluid 650 further in the direction of the distal channel end 270, a conveyance pressure must be built up on the pharmaceutical fluid 650, which pressure overcomes at least the force of the restoring element 420 acting on the ball 40 and thus opens the check valve 400 in terms of fluid conduction.

Figure 4:
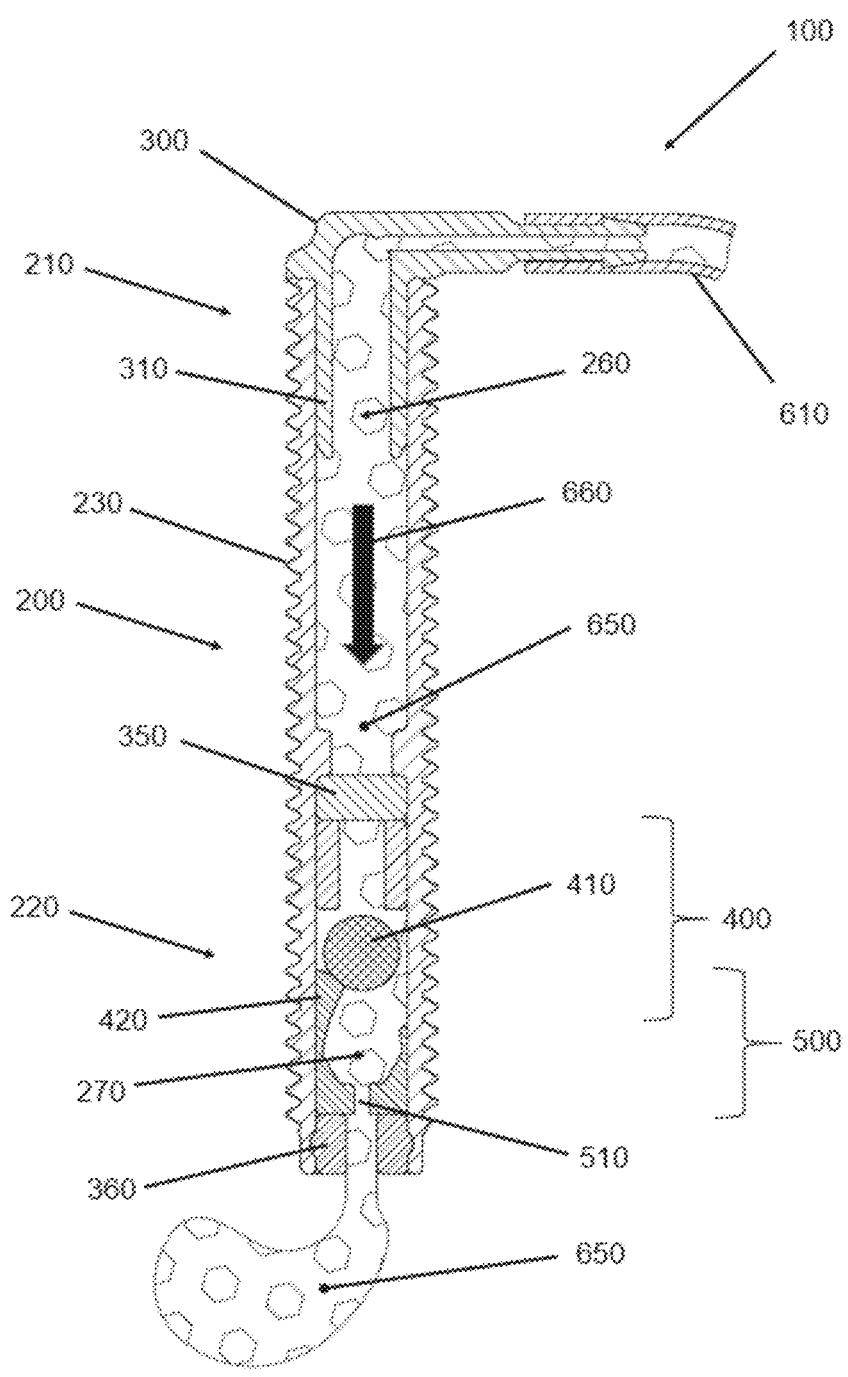

FIG. 4 shows the device 100 from FIGS. 1 to 3, wherein a sufficiently high conveyance pressure 660 (symbolized as an arrow) from the direction of the proximal channel end 260 is exerted on the pharmaceutical fluid 650, in order to displace the ball 410 against the restoring force of the restoring element 420 in the direction of the distal channel end 270. The restoring element 420 is reversibly deformed in the process, and the check valve 400 is opened in terms of fluid conduction. Furthermore, the conveyance pressure 660 is high enough also to reversibly open the gap 510 of the sealing element 500 in terms of fluid conduction. This enables the application of the pharmaceutical fluid 650 from the distal channel end 270. If the conveyance pressure 660 is reduced such that the gap 510, the check valve 400, or the gap 510 and the check valve 400 are again reversibly closed in terms of fluid conduction, the application of the pharmaceutical fluid 650 stops within a few moments, for example within one second or less.

Figure 5:
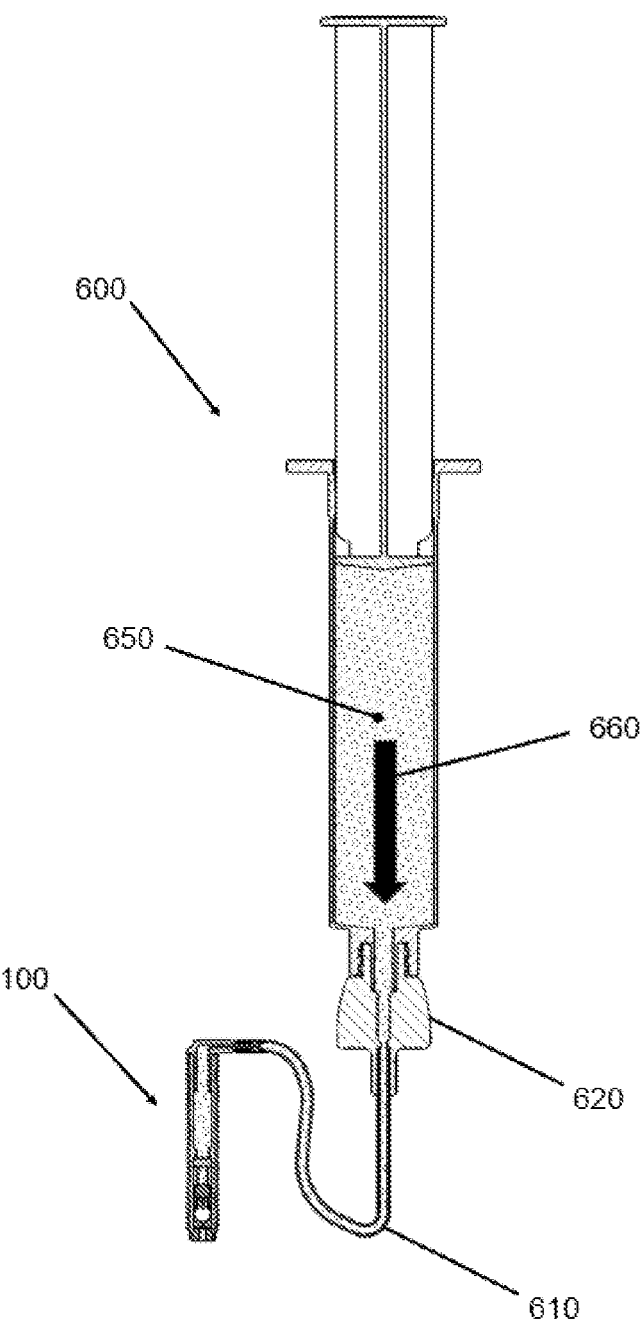

FIG. 5 shows the device 100 from FIGS. 1 to 4 connected in terms of fluid conduction to a reservoir 600 for a pharmaceutical fluid 650 in the form of a syringe. In this case, the device 100 is connected in terms of fluid conduction to the reservoir 600 via a tube 610 and an adapter 620 in the form of a Luer system. By actuating the syringe, a conveyance pressure 660 can be built up on the pharmaceutical fluid 650, and the latter can be applied to a desired location by the device 100.

Figure 6:
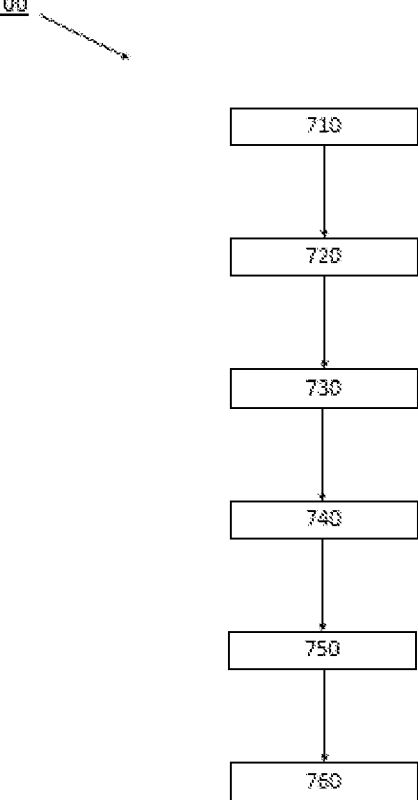

FIG. 6 shows a flow chart of a method for applying a pharmaceutical fluid 650 by means of the device 100, comprising steps 710 to 760. The device 100 comprises the hollow cylindrical body 200 surrounding the channel 250 extending through the body 200 from the proximal body end 210 to the distal body end 220 of the body 200, wherein the outer surface of the body 200 at least partially has the external thread 230, the connecting element 300 arranged at the proximal body end 210 can be reversibly connected in terms of fluid conduction via the proximal channel end 260 of the channel 250 to a reservoir 600 for the pharmaceutical fluid 650, wherein the check valve 400 that is arranged in the channel 250 and is configured to be fluid-impermeable in the direction of the proximal channel end 260, and the sealing element 500 arranged in the channel 250 distal to the check valve 400, which sealing element closes the distal channel end 270 of the channel 250 in terms of fluid conduction, and, when pressure 660 is applied to the pharmaceutical fluid 650 from the direction of the proximal channel end 260, the gap 510 can be reversibly opened in terms of fluid conduction, such that the pharmaceutical fluid (650) can be applied from the distal channel end (270).

In step 710, the device 100 is implanted, in particular into a bone tissue of a patient in spatial proximity to a joint, for example into a condyle of a corresponding bone.

In step 720, the device 100 is connected in terms of fluid conduction to a reservoir 600 for the pharmaceutical fluid 650. This can take place, for example, via a tube 610. The fluid-conducting connection can take place already prior to or only after implantation in step 710, wherein a connection that takes place after implantation is preferred.

In step 730, a conveyance pressure 660 of at least 5 N/cm$^2$ is built up on the pharmaceutical fluid 650 from the direction of the proximal channel end 260. This conveyance pressure 660 is sufficient to open the check valve 400 and the sealing element 500, in particular the gap 510 in the sealing element 500, in terms of fluid conduction at step 740. If the conveyance pressure 660 is less than 5 N/cm$^2$, at least the gap 510 in the sealing element 500 remains closed in terms of fluid conduction and the pharmaceutical fluid 650 is not discharged from the device 100, in particular the distal channel end 270 of the device 100. Said limit value of the conveyance pressure 660 ensures that there is no unintentional and uncontrolled application of the pharmaceutical fluid 650 from the device 100, which could result in negative effects for the patient.

In step 750, the fluid-conducting opening of the gap 510 results in the dispensing of the pharmaceutical fluid 650 from the same. The dispensing of the pharmaceutical fluid 650 continues as long as the conveyance pressure 660 is above the limit value of 5 N/cm$^2$ or until the pharmaceutical fluid 650 is completely discharged.

In step 760, the conveyance pressure 660 is reduced below the limit value of 5 N/cm$^2$, as a result of which at least the gap 510 is automatically closed again in terms of fluid conduction and the application of the pharmaceutical fluid 650 is terminated.

The method 700 can be performed as frequently as desired.

REFERENCE SIGNS

100 Device
200 Hollow cylindrical body
210 Proximal body end
220 Distal body end
230 External thread
250 Channel
255 Channel constriction
260 Proximal channel end
270 Distal channel end
300 Connecting element
310 Connecting element section
350 Filter element
360 Sleeve
365 Tongue-and-groove connection
400 Check valve
410 Ball
420 Restoring element
500 Sealing element
510 Gap
600 Reservoir
610 Tube
620 Adapter
650 Pharmaceutical fluid
660 Application of pressure
700 Method for applying a pharmaceutical fluid
710 Implanting
720 Connecting in terms of fluid conduction
730 Building up of a conveyance pressure
740 Opening in terms of fluid conduction
750 Dispensing
760 Closing in terms of fluid conduction

The invention claimed is:

1. A device for applying a pharmaceutical fluid comprising:
   a hollow cylindrical body, which surrounds a channel that extends through the body from a proximal body end to a distal body end of the body,
   wherein an outer surface of the body has at least partially an external thread, and comprising a connecting element arranged at the proximal body end, via which a proximal channel end of the channel can be reversibly connected in terms of fluid conduction to a reservoir for the pharmaceutical fluid,
   wherein a check valve that is arranged in the channel and is fluid-impermeable in a direction of the proximal channel end, and a sealing element arranged in the channel distal to the check valve, which closes a distal channel end of the channel in terms of fluid conduction and which has a gap that can be reversibly opened in terms of fluid conduction when pressure is applied to the pharmaceutical fluid from the direction of the proximal channel end, such that the pharmaceutical fluid can be applied from the distal channel end.

2. The device according to claim 1, wherein the gap reversibly opens in terms of fluid conduction upon the application of pressure greater than 5 N/cm$^2$.

3. The device according to claim 1, wherein the check valve is a ball check valve comprising a ball and a restoring element.

4. The device according to claim 3, wherein the restoring element and the sealing element are configured in one piece.

5. The device according to claim 1, wherein a filter element is arranged in the channel.

6. The device according to claim 5, wherein the filter element is arranged in the channel proximally to the check valve.

7. The device according to claim 5, wherein the filter element is a microporous filter plate.

8. The device according to claim 7, wherein the microporous filter plate has pores with an average pore diameter of less than 40 μm.

9. The device according to claim 1, wherein a hollow cylindrical sleeve is arranged in the channel distally to the sealing element, in order to prevent the discharging of the sealing element from the distal channel end during the application of the pharmaceutical fluid.

10. The device according to claim 1, wherein the proximal channel end is designed to be polygonal, and the connecting element is equipped with a polygonal connecting element section, in order to reversibly connect in terms of fluid conduction the connecting element to the proximal channel end by inserting the connecting element section into the proximal channel end.

11. The device according to claim 10, wherein the proximal channel end has a larger axial extension than the connecting element section, such that, after removal of a part of the proximal channel end, the connecting element can be reversibly connected in terms of fluid conduction to a part of the proximal channel end remaining on the device by inserting the connecting element section into the remaining proximal channel end.

12. The device according to claim 1, wherein the body comprises a metal and/or a polymer.

13. A method for applying a pharmaceutical fluid by means of a device, said device comprising:
   a hollow cylindrical body, which surrounds a channel that extends through the body from a proximal body end to a distal body end of the body, wherein an outer surface of the body has at least partially an external thread, and comprising a connecting element arranged at the proximal body end, via which a proximal channel end of the channel can be reversibly connected in terms of fluid conduction to a reservoir for the pharmaceutical fluid, wherein a check valve that is arranged in the channel and is fluid-impermeable in a direction of the proximal channel end, and a sealing element arranged in the channel distal to the check valve, which closes a distal channel end of the channel in terms of fluid conduction and which has a gap that can be reversibly opened in terms of fluid conduction when pressure is applied to the pharmaceutical fluid from the direction of the proximal channel end, such that the pharmaceutical fluid can be applied from the distal channel end;

said method for applying the pharmaceutical fluid by means of the device, comprising the following steps:

a. Implanting of the device;

b. Connecting in terms of fluid conduction of the device to a reservoir for the pharmaceutical fluid;

c. Building up of a conveyance pressure on the pharmaceutical fluid from the direction of the proximal channel end of greater than 5 N/cm$^2$;

d. Opening in terms of fluid conduction of the gap in the sealing element by the action of the conveyance pressure;

e. Dispensing of the pharmaceutical fluid from the gap that is open in terms of fluid conduction;

f. Closing in terms of fluid conduction of the gap by reducing the conveyance pressure to 5 N/cm$^2$ or less.

\* \* \* \* \*